United States Patent [19]

Gunjima et al.

[11] Patent Number: 4,514,044
[45] Date of Patent: Apr. 30, 1985

[54] 1-(TRANS-4-ALKYLCYCLOHEXYL)-2-(TRANS-4'-(P-SUBSTITUTED PHENYL)CYCLOHEXYL)ETHANE AND LIQUID CRYSTAL MIXTURE

[75] Inventors: Tomoki Gunjima, Yokohama; Ryutaro Takei, Tokyo, both of Japan

[73] Assignee: Asahi Glass Company Ltd., Tokyo, Japan

[21] Appl. No.: 523,607

[22] Filed: Aug. 16, 1983

[30] Foreign Application Priority Data

Aug. 27, 1982 [JP] Japan .................. 57-147829

[51] Int. Cl.³ .................. C09K 3/34; G02F 1/13; C07C 23/18; C07C 121/00; C07C 13/28; C07C 25/18
[52] U.S. Cl. .................. 350/350 R; 252/299.5; 252/299.63; 260/465 R; 260/465 C; 350/350 S; 570/129; 570/182; 585/20
[58] Field of Search .................. 252/299.63, 299.5; 350/350 R, 350 S; 260/465 R, 465 C; 570/129, 182; 585/20, 25

[56] References Cited

U.S. PATENT DOCUMENTS

| | | | |
|---|---|---|---|
| 4,149,413 | 4/1979 | Gray et al. | 252/299.67 |
| 4,229,315 | 10/1980 | Krause et al. | 252/299.63 |
| 4,261,651 | 4/1981 | Gray et al. | 252/299.63 |
| 4,361,494 | 11/1982 | Osman et al. | 252/299.63 |
| 4,393,258 | 7/1983 | Sato et al. | 252/299.63 |
| 4,400,293 | 8/1983 | Romer et al. | 252/299.63 |
| 4,419,263 | 12/1983 | Praefcke et al. | 252/299.63 |
| 4,431,853 | 2/1984 | Sato et al. | 252/299.63 |
| 4,439,015 | 3/1984 | Rich et al. | 252/299.63 |
| 4,455,443 | 6/1984 | Takatsu et al. | 252/299.63 |

FOREIGN PATENT DOCUMENTS

| | | | |
|---|---|---|---|
| 58512 | 8/1982 | European Pat. Off. | 252/299.63 |
| 72204 | 2/1983 | European Pat. Off. | 252/299.63 |
| 3226051 | 2/1983 | Fed. Rep. of Germany | 252/299.63 |
| 57-163324 | 10/1982 | Japan | 252/299.63 |
| 2092169 | 8/1982 | United Kingdom | 252/299.63 |
| 2107733 | 5/1983 | United Kingdom | 252/299.63 |

OTHER PUBLICATIONS

Gray, G. W., Mol. Cryst. Liq. Cryst., vol. 63, pp. 3–18, (1981).
Gray, G. W., et al., Mol. Cryst. Liq. Cryst., vol. 53, pp. 147–166, (1979).
Praefcke, Klaus von, et al., Chemiker-Zeitung, vol. 104, No. 9, pp. 269–271, (1980).

Primary Examiner—Teddy S. Gron
Attorney, Agent, or Firm—Oblon, Fisher, Spivak, McClelland & Maier

[57] ABSTRACT

A compound represented by the general formula:

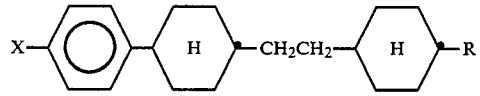

where X is a halogen atom, an alkyl group having from 1 to 8 carbon atoms or a cyano group, and R is an alkyl group having from 1 to 8 carbon atoms.

7 Claims, 3 Drawing Figures

1-(TRANS-4-ALKYLCYCLOHEXYL)-2-(TRANS-4'-(P-SUBSTITUTED PHENYL) CYCLOHEXYL)ETHANE AND LIQUID CRYSTAL MIXTURE

The present invention relates to novel liquid crystal compounds having a high temperature for transition from the nematic phase to the isotropic liquid phase and a wide liquid crystal temperature range.

In the field of display devices, electro-optic devices which meet the requirement for low electric power consumption, are desired. An attention has been drawn to a liquid crystal display cell whereby the orientation of the liquid crystal molecules can be electrically controlled and the electric resistance is very high, thus satisfying the above-mentioned requirement.

The present invention provides a compound represented by the general formula:

(I)

where X is a halogen atom, an alkyl group having from 1 to 8 carbon atoms or a cyano group, R is an alkyl group having from 1 to 8 carbon atoms, and is a 1,4-substituted trans-cyclohexane ring.

The compound represented by the formula I is a liquid crystal compound having a high temperature for transition from the nematic phase to the isotropic liquid phase, a wide liquid crystal temperature range and a low viscosity and is chemically stable against moisture or light. Accordingly, a liquid crystal display cell containing the compound of the formula I is capable of providing a high speed response display within a wide temperature range.

Now, the present invention will be described with reference to the preferred embodiments.

In the accompanying drawings.

In the compound of the formula I, when X is an alkyl group, it is preferably a straight-chain alkyl group, whereby a particularly high clearing point is obtainable. Further, when X is a halogen atom, it is preferably fluorine or chlorine, whereby the viscosity is relatively low. Furthermore, R is preferably a straight-chain alkyl group, whereby a particularly high clearing point is obtainable.

Where X or R is an alkyl group, if the carbon number is small, the liquid crystal temperature range is generally narrow, and if the carbon number is large, the viscosity tends to be high. Therefore, the carbon number is usually from 1 to 8, preferably from 2 to 6.

The compound of the present invention may be used alone or in the form of a mixture for a liquid crystal display device. However, it is usually preferred to use it as a liquid crystal mixture having a wide liquid crystal temperature range. In a case where X and/or R is a branched alkyl group, the compound of the formula I is usually used in an amount of from 0.05 to 5% by weight in the mixture.

In a case where R is a straight-chain alkyl group and X is a straight-chain alkyl group, a fluorine atom or a chlorine atom, the clearing point is high, and accordingly the compound may be used in an amount of from 1 to 90% by weight in the mixture.

In the above-mentioned mixture, the components other than the compound of the formula I of the present invention, may vary depending upon the particular purpose and required properties. However, a component showing liquid crystallinity at a high temperature, a low viscosity component for a low temperature application, other components to improve the dielectric anisotropy, a component to impart the cholesteric property, a component having a dichroic property, a component to impart electro conductivity and various other additives may suitably be incorporated.

As specific examples, the following compounds may be mentioned. In the following formulas, R' and R" represent a group such as an alkyl group, an alkoxy group, a halogen atom or a cyano group.

-continued

These compounds are presented merely for the purpose of illustration. The hydrogen atom on the rings may be substituted by a halogen atom, a cyano group or a methyl group. Likewise, the cyclohexane ring or the benzene ring may be replaced by other six-membered ring or five-membered ring, and the linking group between the rings may be varied. Thus, various materials may optionally be used.

The mixture containing the compound of the present invention is practically used by injecting it into a liquid crystal cell.

As a typical liquid crystal cell, there may be mentioned a twisted nematic (TN) type liquid crystal cell. Namely, a transparent electrode made of e.g. $In_2O_3$—$SnO_2$ is formed in a desired pattern on an inside surface of a transparent substrate made of e.g. glass or a plastic and, if necessary, an overcoat of e.g. $SiO_2$ or a polyimide is applied thereon. A substrate formed with a horizontally oriented layer is placed in a face-to-face relationship therewith, and the periphery of the facing substrates is sealed. Then, the liquid crystal is injected into the space between the facing substrates, and the injection inlet is then sealed. Polarizers are laminated on both outer surfaces of the assembly thus obtained. Further, a phase-change type, a guest-host type, a dynamic scattering type or a combination thereof may also be employed.

For the cell structure, various modifications may be employed, for instance, by providing an undercoat layer of e.g. $SiO_2$ or $Al_2O_3$ between the transparent substrate and the transparent electrode, using a reflective electrode, using a double layered electrode, using a colored polarizer, using a color filter, using a semi-conductor substrate or employing a double layered device structure. The cell may be used for various applications, for instance, for watches, electric calculators, measuring devices, meters for automobiles, game devices or computer terminals.

Among the compounds of the present invention, those of the formular I where X is an alkyl group or a halogen atom, may be produced by the following process.

(I)

In the above formulas, X is a halogen atom or an alkyl group, and R is an alkyl group.

First step:
An alkylbenzene or a halobenzene is reacted with cyclohexene and acetyl chloride in the presence of aluminum chloride to obtain a compound of the formula II.

Second step:
The compound of the formula II prepared in the first step is treated with a sodium hypochlorite solution or a sodium hypobromite solution to obtain a compound of the formula III.

Third step:
The compound of the formula III prepared in the second step is chlorinated with a chlorinating agent such as thionyl chloride or phosphorus oxychloride to obtain a compound of the formula IV.

Fourth step:
A Grignard reagent prepared from trans-4-alkylcyclohexylmethyl bromide and magnesium metal, is reacted with the compound of the formula IV prepared in the third step, in tetrahydrofuran to obtain a compound of the formula V.

Fifth step:
The compound of the formula V prepared in the fourth step is reduced by a Wolff-Kishner method using hydrazine or by a Clemmensen method using zinc amalgam and hydrochloric acid, to obtain a compound of the formula I.

The compounds of the formula I where X is a cyano group, may be prepared by the following process.

In the above formulas, R is an alkyl group.

First to fifth steps: a compound of the formula X is prepared in the same manner as in the first to fifth steps of the process for the preparation of the compound of the formula I where X is an alkyl group or a halogen atom, except that benzene was used in place of the alkylbenzene or the halobenzene in the process for the preparation of the compound of the formula I where X is an alkyl group or a halogen atom.

Sixth step:
The compound of the formula X prepared in the fifth step is reacted with oxalic acid dichloride to obtain a compound of the formula XI.

Seventh step:
The compound of the formula XI prepared in the sixth step is reacted with aqueous ammonia to obtain a compound of the formula XII.

Eighth step:
The compound of the formula XII prepared in the seventh step is dehydrated with a dehydration agent such as phosphorus oxychloride to obtain the desired compound of the formula I.

Among the compounds of the present invention, those of the formula I where X is a straight-chain alkyl group may be prepared also from the compound of the formula X, for instance, by the following process.

Sixth step:
The compound of the formula X prepared in the fifth step and an alkane carboxylic acid chloride are reacted in an inert organic solvent such as carbon disulfide in the presence of a Friedel-Crafts catalyst such as aluminum chloride to obtain a compound of the formula XIII.

Seventh step:
The compound of the formula XIII prepared in the sixth step is reduced by a Wolff-Kishner method using hydrazine or by a Clemmensen method using zinc amalgam to obtain a compound of the formula I.

Now, the present invention will be described in further detail with reference to Examples.

EXAMPLE 1

To a mixture of chlorobenzene (1500 g, 13.3 moles) and aluminum chloride (1080 g, 8.1 moles), a mixture of acetyl chloride (473 g, 6.0 moles) and cyclohexene (555 g, 6.8 moles) was dropwise added in about 3 hours while maintaining the temperature at a level of not higher than $-20°$ C. After the dropwise addition, the reaction system was brought to room temperature. After the termination of the generation of hydrogen chloride gas, the reaction mixture was poured into 5 l of 1:1 hydrochloric acid. After separating the organic layer, the aqueous layer was extracted with diethyl ether, and the organic layers thereby obtained were put together and then dried. The solvent was distilled off by an evaporator. The remaining oily substance was distilled under reduced pressure, whereby 1131 g of a fraction having a boiling point of from 120° to 130° C./0.1 mmHg was obtained. To this fraction, 2 l of a 1:1 mixture of methanol and ethanol was added, and the mixture was cooled in a dry ice/methanol bath to obtain crude crystals. The crude crystals were recrystallized from 500 ml of methanol, whereby 165 g of trans-4-(p-chlorophenyl)-1-acetyl-cyclohexane was obtained. The yield was 12%, and the melting point was 74.6° C.

Then, an aqueous sodium hypobromite solution obtained by dropwise addition of bromine (385 g, 2.41 moles) to 1 l of an aqueous solution of sodium hydroxide (264 g, 8.6 moles), was dropwise added to 800 ml of a dioxane solution of trans-4-(p-chlorophenyl)-1-acetyl-cyclohexane (165 g, 0.70 mole). After the dropwise addition, the mixture was stirred for 2 hours at room temperature, and then the neutral organic substances were removed by extraction with ether. The aqueous layer was acidified with hydrochloric acid, whereby colorless crystals were obtained. The crystals were collected by filtration, washed with water and dried, whereupon 160 g of trans-4-(p-chlorophenyl)cyclohexane carboxylic acid was obtained. The yield was 96%, and the melting point was 235° C. (decomposed).

Then, trans-4-(p-chlorophenyl)cyclohexane carboxylic acid (160 g, 0.67 mole) was stirred together with 100 ml of thionyl chloride and 500 ml of carbon tetrachloride at a reflux temperature for one day and a night. Then the solvent was distilled off by an evaporator. The residue was distilled under reduced pressure, whereby trans-4-(p-chlorophenyl)cyclohexane carboxylic acid chloride was obtained as a yellow liquid. The amount was 152 g, the yield was 88%, and the boiling point was 144° C./0.3 mmHg.

Then, in 150 ml of tetrahydrofuran, a Grignard reagent was prepared from trans-4-n-butylcyclohexyl-methyl bromide (18.6 g, 0.08 mole) and magnesium metal (2.0 g, 0.08 g atm.). The reagent thus prepared was dropwise added to a mixture of trans-4-(chlorophenyl)cyclohexane carboxylic acid chloride (20.6 g, 0.08 mole) and 50 ml of tetrahydrofuran while maintaining the temperature at a level of not higher than $-50°$ C. After the dropwise addition, the mixture was stirred for 2 hours, and 100 ml of water was added. The organic layer was separated, and the water layer was extracted with diethyl ether. The organic layers were put together, washed with 20% sodium hydroxide aqueous solution, then washed with water and dried. Then, the solvent was distilled off. The remaining solid was recrystallized twice from hexane, whereupon 8.3 g of a compound of the formula was obtained. The yield was 28%, and the melting point was 74.0° C.

Then, the compound of the formula n-C$_4$H$_9$ (8.3 g, 0.022 mole), 6 ml of hydrazine hydrate and 6 g of potassium hydroxide were heated in 100 ml of diethylene glycol at 190° C. for 12 hours. The reaction mixture was poured into water, then extracted with chloroform and dried. The solvent was distilled off, whereby a yellow solid remained. This solid was recrystallized twice from ethanol, whereupon 7.3 g of a desired compound of the formula was obtained. The yield was 92%, and this compound was found to have a nematic phase in a range of from 54.3° C. to 149.2° C. by the observation under a polarizing microscope with a hot stage.

The ¹H NMR spectrum of this compound was as follows.

¹H NMR (CDCl₃ solvent, TMS internal standard): δ (ppm): 7.3-7.0; A₂B₂ pattern; 4H; 1.6-0.7; complex m.: 33H.

Figure 1:
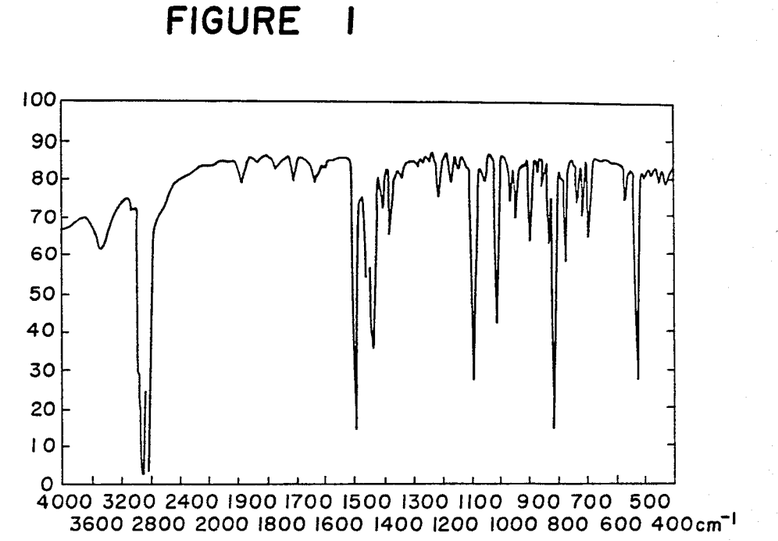
FIGS. 1 to 3 show IR spectra of the compounds obtained in the Examples of the present invention.

The KBr tablet IR spectrum of this compound is shown in FIG. 1.

EXAMPLE 2

A series of operations were conducted in the same manner as in Example 1 except that fluorobenzene was used instead of chlorobenzene in Example 1, whereby the following compounds were obtained.

Trans-4-(p-fluorophenyl)-1-acetylcyclohexane, yield: 14%, melting point: 51.2° C.

Trans-4-(p-fluorophenyl)cyclohexane carboxylic acid, yield: 91%, melting point 201° C. (decomposed).

Trans-4-(p-chlorophenyl)cyclohexane carboxylic acid chloride, yield: 91%, boiling point: 120° C./0.3 mmHg.

A compound of the formula yield: 25%, melting point: 62.4° C.
A compound of the formula yield: 85%.

This compound was found to have a nematic phase in a range of from 72.3° C. to 126.5° C.

The ¹H, ¹⁹F NMR spectra of this compound were as follows.

¹H NMR (CDCl₃ solvent, TMS internal standard) δ ppm: 7.3-6.8; complex m.: 4H; 2.6-0.7; complex m.: 33H.

¹⁹F NMR (CDCl₃ solvent, CFCl₃ internal standard): Φ* (ppm): 116.5; t(J=9 Hz) of t(J=5 Hz).

Figure 2:
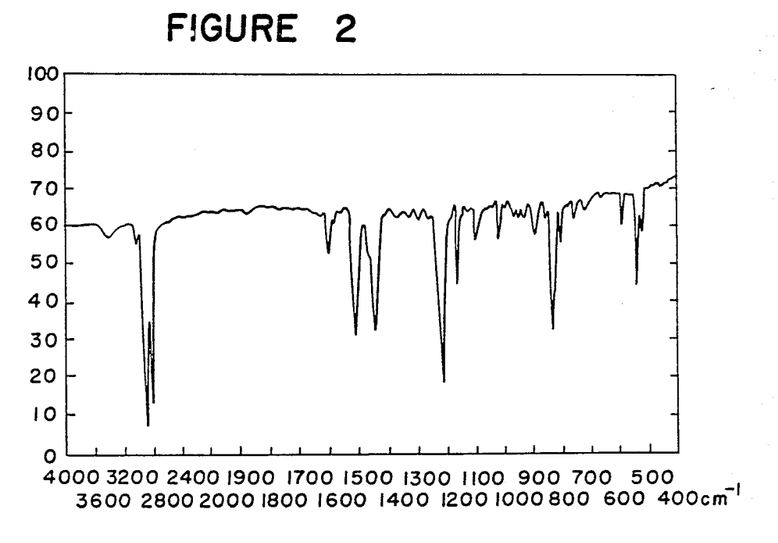

The KBr tablet IR spectrum of this compound is shown in FIG. 2.

EXAMPLE 3

A series of operations were conducted in the same manner as in Example 1 except that benzene was used instead of chlorobenzene in Example 1, whereby the following compounds were obtained.

Trans-4-phenyl-1-acetylcyclohexane, yield: 27%.

Trans-4-phenylcyclohexane carboxylic acid, yield: 90%.

Trans-4-phenylcyclohexane carboxylic acid chloride, yield: 87%, boiling point: 140° C./0.6 mmHg.

A compound of the formula yield: 36%, melting point: 68.9° C.
A compound of the formula yield: 83%, melting point: 54.0° C.

Then, a solution obtained by dissolving the compound of the formula (65.2 g, 0.2 mole) in 280 ml of carbon disulfide, was dropwise added to a mixture of 29.2 g of anhydrous aluminum chloride, 27.8 g of oxalic acid dichloride and 280 ml of carbon disulfide at 15° C. in 30 minutes, and then the mixture was stirred for further 30 minutes and then heated for 1 hour under reflux.

The reaction mixture was poured into a mixture of ice and concentrated hydrochloric acid (5:1) and decomposed. The mixture was extracted with toluene, and 300 ml of 20% KOH was added to the extracted toluene layer. The mixture was refluxed for 3 hours under heating. The reaction mixture was neutralized with hydrochloric acid. The toluene layer was separated, and toluene was distilled off by a rotary evaporator, whereby 41.4 g of a compound of the formula was obtained. Yield: 56%. IR$_{vc=o}^{KBr}$: 1680 cm⁻¹.
A compound of the formula

(37.0 g, 0.1 mole) thus obtained was mixed with 50 ml of thionyl chloride and 200 ml of benzene, and the mixture was refluxed for 5 hours under heating. Then, the excess thionyl chloride and benzene were distilled off by a rotary evaporator, whereby a compound of the formula

IR$_{vc=o}^{KBr}$: 1770 cm⁻¹.

A benzene solution of the above-mentioned acid chloride was dropwise added to 200 ml of concentrated aqueous ammonia at 5° C., and the formed precipitates were collected by filtration, whereby 31 g of a compound of the formula was obtained. Yield: 82%. Melting point: 265.6° C.
The compound of the formula (19 g, 0.05 mole) thus obtained was suspended in 50 ml of chlorobenzene. This suspension was added to a mixture of 7.5 g of pyridine, 35 ml of chlorobenzene and 8 g of phosphorus oxychloride at 0° C. in about 30 minutes, and the mixture was heated to 55° C. in 30 minutes and maintained at this temperature for further 1 hour. After the reaction, the reaction mixture was poured on ice to decompose the excess phosphorus oxychloride. The oil layer was extracted with benzene, and the extracted solution was dried over anhydrous magnesium sulfate. Then, a low boiling fraction was distilled off by a rotary evaporator, whereby a solid substance was obtained. The solid substance was recrystallized from hexane and then purified by chromatography by using alumina as the fixed layer and toluene as the developer. The purified product was further recrystallized from hexane, whereby 13.4 g of a colorless compound of the formula was obtained. Yield: 74%.

This compound was found to show a nematic phase within a range of from 63.5° C. to 189.8° C.

The $^1$H NMR (CDCl$_3$ solvent, TMS internal standard) of this compound was as follows.

δ (ppm): 0.7-2.6; complex m: 33H; 7.2-7.7; A$_2$B$_2$ pattern: 4H.

Figure 3:
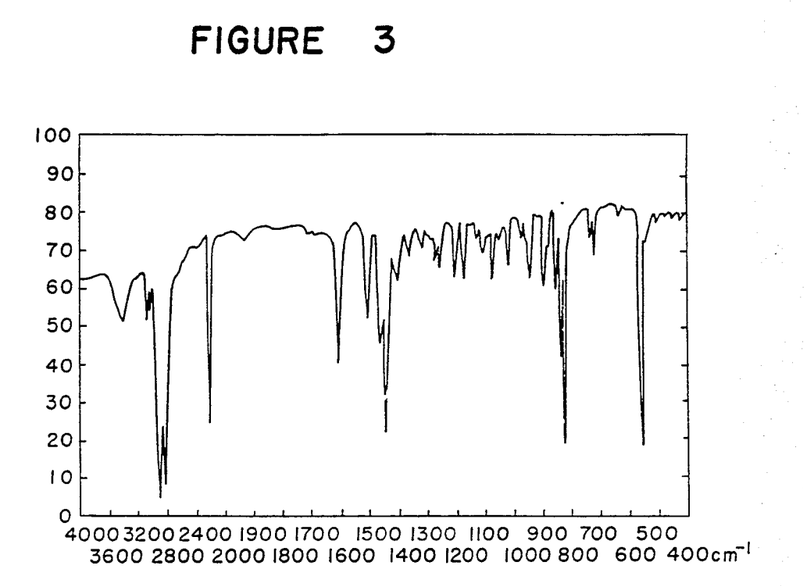

The IR spectrum (KBr tablet) of this compound is shown in FIG. 3.

EXAMPLE 4

A compound of the formula was prepared in the same manner as in Example 3 except that trans-4-n-propylcyclohexylmetylbromide was used instead of trans-4-n-butylcyclohexylmethylbromide in Example 3. Melting point: 67.2° C.

The compound of the formula (40.0 g, 0.13 mole) and anhydrous aluminum chloride (21 g, 0.16 mole) were mixed in 300 ml of carbon disulfide. To this mixture, propionic acid chloride (14.8 g, 0.16 mole) was dropwise added at 15° C. After the dropwise addition, the mixture was stirred for 4 hours at room temperature. The reaction mixture was poured into 20% dilute hydrochloric acid, then extracted with ether and dried, and the solvent was distilled off, whereby yellow crystals were obtained. The crystals were recrystallized from hexane (300 ml), whereby a compound of the formula was obtained. Amount: 36.0 g. Yield: 77%. Melting point: 88.4° C.

Then, the compound of the formula (36.0 g, 0.098 mole), 55 ml of hydrazine hydrate and 55 g of potassium hydroxide was heated in 500 ml of diethylene glycol at 190° C. for 12 hours. The mixture was poured into water, then extracted with chloroform and dried, and the solvent was distilled off. The remaining solid was recrystallized twice from ethanol, whereby a desired compound of the formula was obtained. Amount: 30.8 g. Yield: 88%.

From the observation under a polarizing microscope with a hot stage, this compound was found to have a smectic phase at room temperature, transfer at 141.8° C. from the smectic phase to a namatic phase and further transfer at 144.0° C. from the nematic phase to isotropic liquid phase. The $^1$H NMR of this compound was as follows.

$^1$H NMR (CDCl$_3$ solvent, TMS internal standard): δ 7.05; s: 4H; δ 2.55; t J=7 Hz: 2H; δ 2.6-0.7; complex m: 36H.

EXAMPLES 5 TO 14

In the same manner as in Example 1, the following compounds were obtained.

-continued

Nematic phase: 77.0° C.–155.0° C.
$^1$H NMR (CDCl$_3$ solvent, TMS internal standard): δ 7.3–7.0; A$_2$B$_2$ pattern: 4H; 2.6–0.7; complex m: 3H.

Namatic phase: 64.3° C.–130.2° C.
$^1$H NMR (CDCl$_3$ solvent, TMS internal standard): δ 7.3–6.8; complex m: 4H; 2.6–0.7; complex m: 31H.
$^{19}$F NMR (CDCl$_3$ solvent, CFCl$_3$ internal standard): Φ* 116.5; t(J=9 Hz) of t(J=5 Hz).

EXAMPLES 15 TO 17

In the same manner as in Example 3, the following compounds were obtained.

Namatic phase: 86.3° C.–197.1° C.
$^1$H NMR (CDCl$_3$ solvent, TMS internal standard): δ 7.7–7.2; A$_2$B$_2$ pattern: 4H; 2.6–0.7; complex m: 31H.

EXAMPLE 18

By using the compound of the formula n-C$_5$H$_{11}$—[H]—[ring]—[ring]—CN as a Comparative Example, the viscosities of the compounds of the Examples 1 and 2 were compared. A mixture (hereinafter referred to as "parent liquid crystal A") comprising 25% by weight of trans-1-n-propyl-4-(4'-ethoxyphenyl)cyclohexane, 20% by weight of trans-1-n-propyl-4-(4'-n-butoxyphenyl)cyclohexane and 55% by weight of liquid crystal ZLI-1083 manufactured by Merck & Co., Inc. showed a viscosity of 45.3 cSt at 0° C. A mixture comprising 90% by weight of this parent liquid crystal A and 10% by weight of each compound showed a viscosity at 0° C. as shown in Table 1.

TABLE 1

| Compound | | Viscosity (cSt) |
|---|---|---|
| Example 1 | Cl—[ring]—[H]—CH$_2$CH$_2$—[H]—n-C$_4$H$_9$ | 48.4 |
| Example 2 | F—[ring]—[H]—CH$_2$CH$_2$—[H]—n-C$_4$H$_9$ | 46.6 |
| Comparative Example | n-C$_5$H$_{11}$—[H]—[ring]—[ring]—CN | 55.9 |

It is evident from the Table that liquid crystal mixtures containing the compound of the present invention showed a low viscosity.

Now, the compounds of the present invention as applied to a twisted nematic (TN) liquid crystal display device will be described.

The TN liquid crystal display device had a construction wherein a pair of electrode-laminated transparent glass substrates subjected to homogeneous orientation treatment by rubbing them with a cotton cloth in one direction in accordance with a conventional method, were disposed to face each other with a distance of 8 μm and with the rubbing directions arranged to be perpendicular to each other. A liquid crystal was injected into the space between the substrates, and a pair of polarizers were bonded thereto. To this device, an AC voltage of 100 Hz was applied, and the change of the percent transmission in the direction inclined by 10° towards the direction for the greatest contrast from the normal line of the substrates, was measured, whereby the applied voltage at which the percent transmission changed by 10% relative to that at the time when no voltage was applied, was defined as a threshold voltage $V_{10}$.

With respect to mixtures of a parent liquid crystal A with the compounds of the present invention, $V_{10}$ at $-20°$ C. and the temperature Tc at which the nematic phase changed into the isotropic liquid, are shown in Table 2.

mode, a twisted nematic (TN) mode or a guesthost (GH) mode.

The compound of the present invention have a high temperature for the transition from the nematic phase to isotropic liquid phase and a wide liquid crystal temperature range, and they are chemically stable and yet have a low viscosity. Thus, they are expected to be quite useful. Liquid crystal display devices containing the compound of the present invention are capable of providing a display which is stable within a wide temperature range and exhibit quick response. Accordingly, they may be used for various applications including an application to vehicles.

We claim:

1. A compound represented by the general formula:

where X is a halogen atom, an alkyl group having from 1 to 8 carbon atoms or a cyano group, and R is an alkyl group having from 1 to 8 carbon atoms.

2. The compound according to claim 1, wherein R is

TABLE 2

| Compounds | | Contents (% by weight) | Tc (°C.) | $V_{10}(V)$ |
|---|---|---|---|---|
| Example 1 | Cl—⬡—H—CH₂—CH₂—H—n-C₄H₉ | 7.0 | 44.2 | 3.36 |
| Example 2 | F—⬡—H—CH₂—CH₂—H—n-C₄H₉ | 7.0 | 42.7 | 3.20 |
| Example 3 | NC—⬡—H—CH₂—CH₂—H—n-C₄H₉ | 10.0 | 50.8 | 3.43 |
| Parent liquid crystal A | — | — | 37.4 | 3.16 |

From the results shown in Table 2, it is evident that the compounds of the present invention are capable of substantially raise Tc without substantially raising the threshold voltage.

The compounds of the present invention may be used alone or in combination as a mixture of two or more, or may be combined with other nematic, cholesteric or smectic liquid crystals dichroic dyestuffs, to form a liquid crystal mixture. Such a liquid crystal or liquid crystal mixture is sealed in the space between transparent substrates having an electrode of a desired configuration to form a liquid crystal display device.

Further, this device may be provided with various undercoats, overcoats for controlling the orientation, polarizers, filters or reflective layers, as the case requires. It may be made in the form of a cell having multi liquid crystal layers or may be combined with other display devices. Further, a semi-conductor substrate may be used, or a light source may be used. Thus, various modifications may be employed.

As a mode for operating the liquid crystal display device, various modes which are commonly employed in the field of liquid crystal display devices may be employed, for instance, a dynamic scattering (DSM)

a straight-chain alkyl group having from 1 to 8 carbon atoms.

3. The compound according to claim 2, wherein X is a fluorine atom, a chlorine atom, a straight-chain alkyl group having from 1 to 8 carbon atoms or a cyano group.

4. A liquid crystal mixture containing a compound represented by the general formula:

where X is a halogen atom, an alkyl group having from 1 to 8 carbon atoms or a cyano group, and R is an alkyl group having from 1 to 8 carbon atoms.

5. The liquid crystal mixture according to claim 4, which contains from 0.05 to 5% by weight of the compoound of the formula I where X and/or R is a branched alkyl group.

6. The liquid crystal mixture according to claim 4, which contains from 1 to 90% by weight of the compound of the formula I where R is straight-chain alkyl group having from 1 to 8 carbon atoms, and X is a halogen atom, a straight-chain alkyl group having from 1 to 8 carbon atoms or a cyano group.

7. A liquid crystal display cell which comprises a pair of electrodelaminated transparent substrates disposed in a spaced relation with each other with the respective electrode surfaces facing to each other and sealed along the periphery of the facing substrates, and a liquid crystal composition injected and sealed in the space between the pair of substrates, said composition comprising a compound represented by the general formula:

where X is a halogen atom, an alkyl group having from 1 to 8 carbon atoms or a cyano group, and R is an alkyl group having from 1 to 8 carbon atoms.

* * * * *